United States Patent [19]

Guillaume et al.

[11] Patent Number: 4,650,811

[45] Date of Patent: Mar. 17, 1987

[54] ETHENYLPHENOL-INDOLES HAVING ANTIARYTHMIC UTILITY

[75] Inventors: Jacques Guillaume, Le Pré-Saint-Gervais; François Clémence; Neil L. Brown, both of Paris, all of France

[73] Assignee: Roussel Uclaf, Paris, France

[21] Appl. No.: 691,163

[22] Filed: Jan. 14, 1985

[30] Foreign Application Priority Data

Jan. 13, 1984 [FR] France ............................. 84 00492

[51] Int. Cl.[4] .................... C07D 209/12; A61K 31/40
[52] U.S. Cl. .................................... 514/415; 514/418; 514/239; 514/253; 514/323; 548/469; 548/486; 546/201; 544/143; 544/144; 544/373
[58] Field of Search ................ 548/469, 486; 514/415, 514/418, 323, 239, 253; 546/201; 544/143, 144, 373

[56] References Cited

U.S. PATENT DOCUMENTS 4,333,951 6/1982 Walsh ............................. 514/538 X

FOREIGN PATENT DOCUMENTS 2528043 12/1983 France .

Primary Examiner—Donald G. Daus
Assistant Examiner—William A. Teoli, Jr.
Attorney, Agent, or Firm—Bierman and Muserlian

[57] ABSTRACT

Novel ethenylphenol indoles of the formula

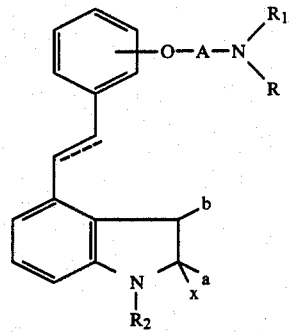

wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, methylthio, —$CF_3$, —$NH_2$ and —$NO_2$ or R and $R_1$ together with the nitrogen atom form an optionally unsaturated heterocycle optionally containing a second heteroatom selected from the group consisting of —O—, —S— and

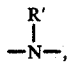

R' is hydrogen or alkyl of 1 to 5 carbon atoms, a together with X is =O and b is hydrogen or a together with b is a carbon-carbon bond and X is hydrogen, the dotted line indicates the possibility of a double bond with the compounds having the trans configuration if a double bond, A is selected from the group consisting of

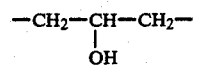

and —$(CH_2)_n$—, n is 2,3,4 or 5, $R_2$ is selected from the group consisting of hydrogen and alkyl of 1 to 5 carbon atoms with the proviso that R and $R_1$ are not both hydrogen when A is

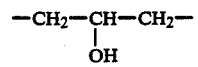

and their non-toxic, pharmaceutically acceptable acid addition salts having anti-arrhythmic and anti hypertensive properties and the property of blocking slow calcium-sodium channels and novel intermediates.

27 Claims, No Drawings

ETHENYLPHENOL-INDOLES HAVING ANTIARYTHMIC UTILITY

STATE OF THE ART

U.S. Pat. No. 4,333,951 describes 2-amino-6-biphenylacetic acids and their esters and metal salts having muscle relaxant and anti-inflammatory activity and certain indole intermediates. Copending commonly assigned U.S. patent application Ser. No. 498,835 filed May 27, 1983 describes 1,3-dihydro-4-(1-hydroxy-2-aminoethyl)-2H-indol-2-ones having antihypertensive and hypotensive activity.

OBJECTS OF THE INVENTION

It is an object of the invention to provide the novel indoles of formula I and their non-toxic, pharmaceutically acceptable acid addition salts and a novel process and novel intermediates for their preparation.

It is another object of the invention to provide anti hypertensive compositions and a novel method of inducing anti hypertensive activity in warm-blooded animals.

These and other objects and advantages of the invention will become obvious from the following detailed description.

THE INVENTION

The novel compounds of the invention are selected from the group consisting of ethenylphenol indoles of the formula

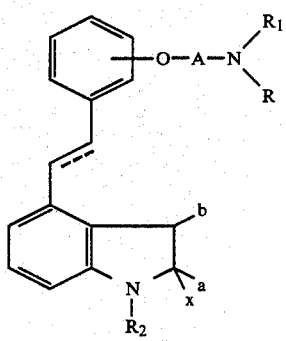

wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, methylthio, —CF$_3$, —NH$_2$ and —NO$_2$ or R and $R_1$ together with the nitrogen atom form an optionally unsaturated heterocycle optionally containing a second heteroatom selected from the group consisting of —O—, —S— and

R' is hydrogen or alkyl of 1 to 5 carbon atoms, a together with X is =O and b is hydrogen or a together with b is a carbon-carbon bond and X is hydrogen, the dotted line indicates the possibility of a double bond with the compounds having the trans configuration if a double bond, A is selected from the group consisting of

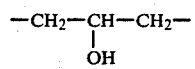

and —(CH$_2$)$_n$—, n is 2,3,4 or 5, $R_2$ is selected from the group consisting of hydrogen and alkyl of 1 to 5 carbon atom with the proviso that R and $R_1$ are not both hydrogen when A is

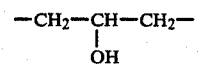

and their non-toxic, pharmaceutically acceptable acid addition salts.

Examples of alkyl of 1 to 5 carbon atoms are methyl, ethyl, propyl, isopropyl, n-butyl, isobutyl, tert.-butyl, n-pentyl and isopentyl. Examples of cycloalkyl of 3 to 7 carbon atoms are cyclopropyl, cyclobutyl, cyclhexyl and preferably cyclopentyl while examples of cycloalkylalkyl of 4 to 7 carbon atoms are cyclobutylmethyl and preferably cyclopropyl methyl. Examples of aralkyl of 7 to 12 carbon atoms are benzyl and phenethyl optionally substituted with 1 to 3 halogen, methyl, ethyl, methoxy, ethoxy, —CF$_3$, methylthio, —NH$_2$ and —NO$_2$. Examples of heterocycles formed from

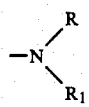

are pyrrolidino, piperidino, morpholino, piperazinyl, methylpiperazinyl, ethylpiperazinyl and propylpiperazinyl.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and arylcarboxylic acids such as benzoic acids.

Among the preferred compounds of formula I are those wherein $R_2$ is hydrogen, A is

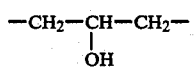

and R and $R_1$ are hydrogen or alkyl of 1 to 5 carbon atoms with at least one not being hydrogen, those wherein $R_2$ is hydrogen, A is —(CH$_2$)$_n$— and R and $R_1$ are hydrogen or alkyl of 1 to 5 carbon atoms, those wherein

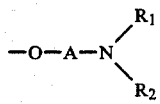

is in the ortho position and those wherein R is hydrogen and a and b form a carbon-carbon bond and their non-toxic, pharmaceutically acceptable acid addition salts.

Examples of preferred compounds of formula I are 1-[1,1-dimethylethylamino]-3-[4-[2-(1H-indol-4-yl)-ethenyl]phenoxy]-2-propanol, 1-[1,1-dimethylethylamino]-3-[2-[2-(1H-indol-4-yl)-ethyl]phenoxy]-2-propanol, 1,3-dihydro-4-[2-[2-3-[1,1-dimethylethylamino]-2-hydroxypropoxy]-phenyl]-ethenyl]2H-indol-2-one and N-(1,1-dimethylethyl)-3-[2-[2-(1H-indol-4-yl)-ethyl]-phenoxy]-propanamine and their non-toxic, pharmaceutically acceptable acid addition salts.

The novel process of the invention for the preparation of the compounds of formula I comprises reacting an indole of the formula

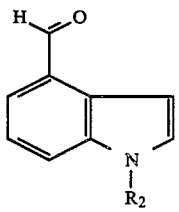

II wherein $R_2$ has the above definition with a hydroxybenzyltriphenylphosphonium halide of the formula

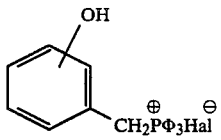

III wherein the hydroxy radical is in position 2-, 3- or 4- and Hal is chlorine or bromine to obtain a derivative of the formula

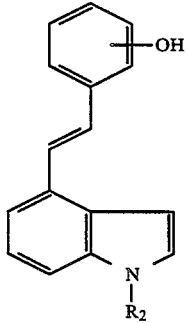

IV reacting the latter either with a halide of the formula

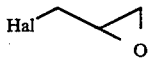

V wherein Hal has the above definition to obtain a derivative of the formula

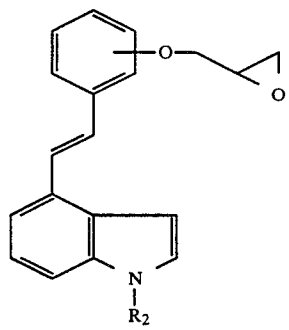

VI and reacting the latter with a primary or secondary amine of the formula

VII wherein R and $R_1$ have the above definition to obtain a product of the formula

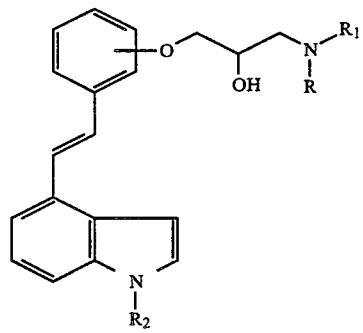

$I_A$ which either is isolated and if desired, salified, or is submitted to a hydrogenation to obtain a product of the formula

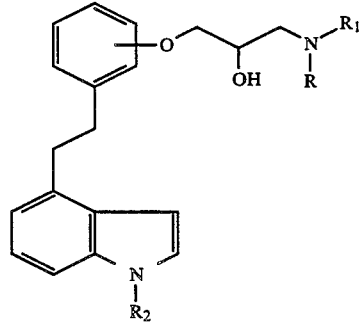

$I_B$ wherein R, $R_1$ and $R_2$ have the above definition which if desired, is salified, or the product of formula IV is reacted with the halide of formula Hal—$(CH_2)_n$—$OR_3$   V' wherein Hal and n have the above definition and $R_3$ is tosyl or hydrogen to obtain a product of the formula

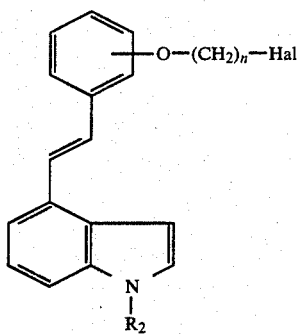

wherein n, Hal and R₂ have the above definitions and reacting the latter with an amine of formula VII to obtain a product of the formula

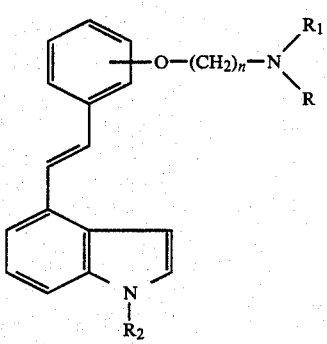

wherein n, R, R₁ and R₂ have the above definitions which either is isolated and, if desired, salified, or is submitted to a hydrogenation to obtain a product of the formula

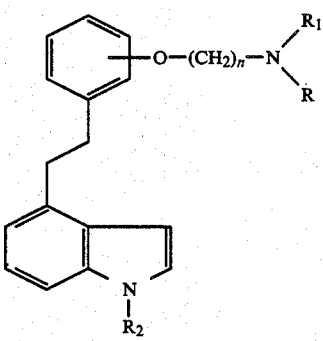

wherein n, R, R₁ and R₂ have the above definitions then, if desired, the products of formula $I_A$, $I_B$, $I'_A$ and $I'_B$ are submitted to the action of a halogenating agent to obtain a product of the formula

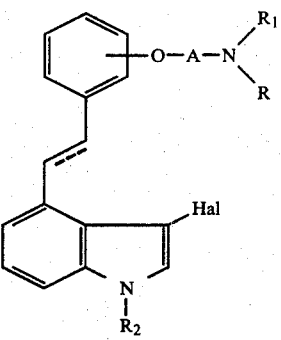

wherein A, Hal, R, R₁, R₂ and the broken line have the above definitions and subjecting the latter to hydrolysis to obtain a product of the formula

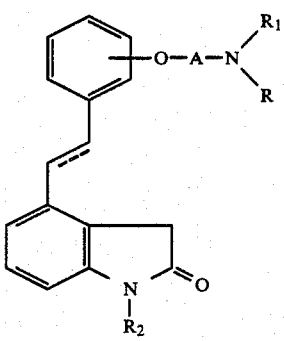

wherein A, R, R₁, R₂ and the broken line have the above definitions which is isolated and if desired, salified.

The reaction of 4-formyl indole with the product of formula III can be carried out directly in a solvent or a mixture of solvents such as hexane or tetrahydrofuran, but preferably in the presence of an organic base such as butyl lithium or an alkali metal alcoholate or an alkali metal amide such as lithium diisopropyl amide.

The reaction of the product of formula IV with the halide of formula V can be carried out in a solvent or a mixture of inert solvents such as tetrahydrofuran, dioxane, dimethylformamide, and particularly acetone and is preferably carried out in the presence of a condensation agent such as a base like sodium hydroxide, triethylamine or an alkali metal carbonate like potassium or sodium carbonate. The opening of the epoxide by the amine of formula VII can be utilized directly in the amine which thus serves as solvent or in a solvent such as an aliphatic alcohol like ethanol.

The reaction of the product of formula IV with the halide of formula V' is preferably carried out in the presence of triphenyl phosphine and diethyl azodicarboxylate if R₃ is hydrogen. If R₃ is tosyl, the reaction preferably takes place in the presence of a base such as sodium or potassium hydroxide or an alkali metal alcoholate like sodium ethylate, or in the presence of an alkali metal hydride like sodium hydride.

The hydrogenation of the products of formulae $I_A$ and $I'_A$ can be effected chemically, for example by hydrazine, or in a catalytic manner, and in this case, hydrogen is utilized in the presence of platinum or palladium, or preferably Raney's nickel.

The halogenation of the products of formulae $I_A$, $I'_A$, $I_B$ and $I'_B$ can, for example, be realized with the brominated complex of pyridine of the formula

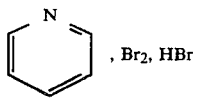, $Br_2$, HBr in the case of bromination. It is also advantageously carried with a N-halo succinimide, preferably N-bromo or N-chloro-succinimide in dioxane or preferably in acetic acid. The product of formula VIII is preferably a chlorinated product.

The hydrolysis of the product of formula VIII is preferably realized by means of a mineral acid such as phosphoric acid, sulfuric acid, or preferably hydrochloric acid in aqueous solution. This solution can be concentrated, but is preferably dilute, for example, a normal solution. In addition, a solvent such as an aliphatic alcohol like ethanol can be used.

In a variations of the process to prepare the product of formula $I'_A$. (a) either a product of formula IV can be reacted with a dihalide of the formula

     V''' wherein Hal has the above definition and Hal' has the significance of Hal to obtain the corresponding halogenated condensation product which is reacted with an amine of the formula

     VII wherein R and $R_1$ have the above definition to obtain the product of formula $I'_A$. (b) or a product of formula IV can be reacted with a halide of the formula

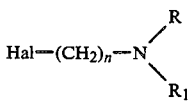     V'''' wherein Hal, R and $R_1$ have the above definitions under similar conditions for the reaction with the halide of formula V to obtain the expected product of formula $I'_A$.

In another variantion when $R_2$ is an alkyl, it can be fixed in the last stage of the process, for example by the action of an alkyl halide (chloride, bromide or iodide) with a product of formula I wherein $R_2$ is hydrogen, preferably in the presence of a base as above.

The starting products of formula II are described notably in J. Org. Chem (1980) Vol. 45, p. 3350 and those following. The products of formula III are known products and their preparation is in particular described in Tetrahedron 1981, Vol. 37, No. 16, p. 2867.

The compounds of formula I present a basic character and the acid addition salts of the derivatives of formula I can with advantage be prepared by reacting a mineral or organic acid in substantially stoichiometrical proportions with the said derivative of formula I. The salts can be prepared without isolating the corresponding bases.

The novel hypertensive and anti-arrhythmic compounds of the invention are comprised of an hypertensively and antiarrhythmically effective amount of at least one compound of formula I and their non-toxic, pharmaceutically acceptable acid addition salts and an inert pharmaceutical carrier or excipient. The compositions may be in the form of tablets, dragees, capsules granules, suppositories or injectable solutions or suspensions.

Examples of suitable excipients are talc, arabic gum, lactose, starch, magnesium stearate, cocoa butter, aqueous and non-aqueous vehicles, animal or vegetable fatty bodies, paraffin derivatives, glycols, various wetting agents, dispersants and emulsifiers and preservatives.

Among the preferred compositions of the invention are those wherein $R_2$ is hydrogen, A is

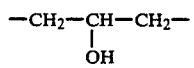

and R and $R_1$ are hydrogen or alkyl of 1 to 5 carbon atoms with at least one not being hydrogen, those wherein $R_2$ is hydrogen, A is $-(CH_2)_n-$ and R and $R_1$ are hydrogen or alkyl of 1 to 5 carbon atoms, those wherein

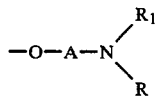

is in the ortho position and those wherein R is hydrogen and a and b form a carbon-carbon bond and their non-toxic, pharmaceutically acceptable acid addition salts.

Especially preferred compositions of the invention are those wherein the active ingredient is selected from the group consisting of 1-[1,1-dimethylethylamino]-3-[4-(2-(1H-indol-4-yl)-ethenyl]phenoxy]-2-propanol, 1-[1,1-dimethylethylamino]3-[2-[2-(1H-indol-4-yl)-ethyl]-phenoxy]2-propanol, 1,3-dihydro-4-[2-[2-[3-[1,1-dimethylethylamino]-2-hydroxypropoxy]phenyl]ethenyl]2H-indol-2-one and N-(1,1-dimethylethyl)-3-[2-[2-(1H-indol-4-yl). ethyl]phenoxy]propanamine and their non-toxic, pharmaceutically acceptable acid addition salts.

The compositions are useful in the treatment of essential arterial hypertension, of hypertension of the fifties, of menopause, of diabetes, of obesity and of plethoric, as well as in the treatment of arterial hypertension in subjects aged or attacked by arteriosclerosis and in the treatment of hypertension of renal origin as well as the treatment of cardiac insufficiency, of angina in all its forms and in the treatment of arrhythmia.

The novel method of the invention for the treatment of hypertension and arrhythmia in warm-blooded animals, including humans, comprises administering to warm-blooded animals an anti hypertensively or anti-arrhythmially effective amount of at least one compound of formula I and their non-toxic, pharmaceutically acceptable acid addition salts. The compounds may be administered orally, rectally or parenterally and the usual daily dose is 0,15 to 7,15 mg/kg depending on the conditions being treated, the compound used and the method of administration. For example, the compound of Example 3 is orally administered at 0.15 to 1.5 mg/kg daily for the treatment of angina.

The compounds of formula I and their acid addition salts also block the slow calcium-sodium channels and some of the compounds of formula I also have α- and-/or β-blocking properties.

The novel intermediates of the invention are those of formula IV.

In the following examples there are described several preferred embodiments to illustrate the invention. However, it should be understodd that the invention is not intended to be limited to the specific embodiments.

EXAMPLE 1

1-[2-[2-(1H-indol-4-yl)-ethenyl]-phenoxy]-3-[isopropyl-amino]-2-propanol and its hydrochloride STEP A: 2-[(1H-indol-4-yl)-ethenyl]-phenol Under an inert atmosphere, 31 g of ortho hydroxybenzyltriphenyl-phosphonium bromide were suspensed in 350 ml of tetrahydrofuran and then over a period of one hour, 86 ml of a 1.6 M solution of butyllithium in hexane were added. The mixture stood for 30 minutes with stirring and then over 30 minutes, a solution of 5 g of 4-formyl-indole in 150 ml of tetrahydrofuran was added. The mixture was stirred for 24 hours and then was diluted with 500 ml of water. Potassium carbonate was added to saturation, and the mixture was extracted with ethyl acetate. The fractions with Rf=0.20 were isolated by chromatography on silica (eluent: methylene chloride) and the crystals obtained were triturated in methylene chloride, then filtered and dried under reduced pressure to obtain 7.4 g of 2-[(1H-indol-4-yl)-ethenyl]-phenol melting at 140° C., and after recrystallization from methylene chloride at 142° C.

STEP B:
4-[2-(2-[(2-oxiranyl)methoxy]-phenyl)-ethenyl]-1H-indole 7.25 g of the product of Step A were refluxed with 150 ml of acetone, 4.4 g of potassium carbonate and 3 ml of epichlorhydrin for 24 hours with stirring under an inert atmosphere. After filtering, the solvent was evaporated at 50° C. under reduced pressure and the fractions with RF=0.40 were recovered by chromatography on silica (eluent: methylene chloride) to obtain 5.8 g of 4-[2-[(2-[(2-oxiranyl)methoxy]-phenyl)-ethenyl]-1H-indole as a yellow oil after elimination of the solvent.

STEP C:
1-[2-[2-(1H-indol-4-yl)-ethenyl]-phenoxy]-3-[isopropyl]-amino]-2-propanol and its hydrochloride 4.8 g of the oil obtained in Step B were stirred under an inert atmosphere for 20 hours in 5.7 ml of isopropylamine and the solvent was evaporated at 50° C. under reduced pressure. The crystals obtained were triturated in petroleum ether (b.p.: 60°–80° C.) and then filtered and dried under reduced pressure. The product was purified by chromatography on silica (eluent:ethyl acetate-triethylamine 9-1) to obtain 5 g of 1-[2-[2-(1H-indol-4-yl)-ethenyl]-phenoxy]-3-[isopropyl]-amino]-2-propanol melting at 110° C.

Formation of the hydrochloride:

The said base was dissolved in 100 ml of ethyl acetate and an excess of a saturated solution of hydrochloric acid in ethyl acetate was added. After concentrating, cooling, filtering and drying under reduced pressure, a product was obtained which was crystallized from 200 ml of isopropanol and 400 ml of methanol at reflux to obtain 4 g of the hydrochloride melting at ≃254° C.

| Analysis: $C_{22}H_{26}N_2O_2HCl$; molecular weight = 386.925 | | | | |
|---|---|---|---|---|
| | % C | % H | % N | % Cl |
| Calculated: | 68.29 | 7.03 | 7.27 | 9.16 |
| Found: | 68.2 | 7.1 | 7.3 | 9.3 |

EXAMPLE 2

1-[(1,1-dimethylethyl)-amino]-3-[2-[2-(1H-indol-4-yl)-ethenyl-]-phonoxy]-2-propanol and its hydrochloride Using the process of Example 1, isopropylamine was replaced with tert-butylamine to obtain 1-[(1,1-dimethylethyl)-amino]-3-[2-[2-(1H-indol-4-yl)-ethenyl]-phenoxy]-2-propanol in its hydrochloride form which melted at ≃230° C.

| Analysis: $C_{22}H_{29}N_2ClO_2$; molecular weight = 400.952 | | | | |
|---|---|---|---|---|
| | % C | % H | % N | % Cl |
| Calculated: | 68.90 | 7.29 | 6.99 | 8.84 |
| Found: | 68.9 | 7.4 | 6.8 | 8.8 |

EXAMPLE 3

1-[(1,1-dimethylethyl)-amino]-3-[4-[2-(1H-indol-4-yl)-ethenyl]-phenoxy]-2-propanol and its hydrochloride STEP A: 4-[(1H-indol-4-yl)-ethenyl]-phenol 31 g of p-hydroxybenzyltriphenylphosphonium bromide ware suspended in 350 ml of tetrahydrofuran under an inert atmosphere, and over one hour 86 ml of a 1.6 M solution of butyllithium in hexane were added thereto. After stirring for 30 minutes, a solution of 5 g of 4-formyl-indole in 100 ml of tetrahydrofuran was added over 30 minutes, and the mixture was stirred for 24 hours. After dilution with 500 ml of water, the mixture was extracted with ethyl acetate. The fractions with an Rf=0.15 were isolated by chromatography on silica (eluent:methylene chloride) were triturated with petroleum ether (b.p. 60°–80° C.), filtered and dried under reduced pressure to obtain 7 g of 4-[(1H-indol-4-yl)-ethenyl]-phenol melting at ≃145° C.

STEP B:
4-[2-[4-[(2-oxiranyl)-methoxy]-phenyl]-ethenyl]-1H-indol

A mixture of 5.8 g of the product of Step A, 120 ml of acetone, 3.6 g of potassium carbonate and 9.6 ml of epichlorhydrin was refluxed for 24 hours with stirring under an inert atmosphere. Then, 9.6 ml of epichlorhydrin were added and reflux was continued for 5 hours. After filtering, the solvent was evaporated under reduced pressure at 60° C., and the fractions with Rf=0.35 were recovered by chromatography on silica (eluent:methylene chloride) to obtain 5.25 g of 4-[2-[4-[(2-oxiranyl)-methoxy]-phenyl]-ethenyl]-1H-indole melting at ≃128° C.

STEP C:
1-[(1,1-dimethylethyl)-amino]-3-[4-[2-(1H-indol-4-yl)-ethenyl]-phenoxy]-2-propanol and its hydrochloride 7.5 g of the product of Step B and 27 ml of tert-butylamine were refluxed with stirring under an inert atmosphere for 1 hour in 100 ml of ethanol. After evaporating the solvent at 50° C. under reduced pressure and purifying the residue by chromatography on silica (eluent: chloroform-acetone-triethylamine 6-3-1), 9.4 g of 1-[(1,1-dimethylethyl)-amino]-3][4-[2-(1H-indol-4-yl)-ethenyl]-phenoxy]-2-propanol were obtained.

Formation of the hydrochloride 9.4 g of the said base were dissolved in 400 ml of isopropanol, and an excess of a saturated solution of hydrochloric acid in ethyl acetate was added thereto. After concentrating, cooling, filtering and drying under reduced pressure, 9.6 g of crude product were obtained. 5 g of the crude product were crystallized from 300 ml of isopropanol and 200 ml of methanol at reflux to obtain 4.5 g of the hydrochloride melting at ≃256° C.

| Analysis: $C_{23}H_{28}N_2O_2$, HCl; molecular weight = 400.952 | | | | |
|---|---|---|---|---|
| | % C | % H | % N | % Cl |
| Calculated: | 68.90 | 7.29 | 6.99 | 8.84 |
| Found: | 68.9 | 7.4 | 7.0 | 8.9 |

EXAMPLE 4

1-[4-[2-(1H-indol-4-yl)-ethenyl]-phenoxy]-3-[1-methylethyl)-amino]-2-propanol and its hydrochloride Using the process of Example 1, o-hydroxybenzytriphenyl phosphonium was replaced with p-hydroxybenzyltriphenyl phosphonium to obtained 1-[4-[2-(1H-indol-4-yl)-ethenyl]-phenoxy]-3-[1-methylethyl)-amino]-2-propanol and its hydrochloride whose hydrochloride melted at ≃250° C.

| Analysis: $C_{22}H_{27}N_2ClO_2$; molecular weight = 386.925 | | | | |
|---|---|---|---|---|
| | % C | % H | % N | % Cl |
| Calculated: | 68.29 | 7.03 | 7.27 | 9.16 |
| Found: | 68.3 | 7.1 | 7.1 | 9.2 |

EXAMPLE 5

1,3-dihydro-4-[2-[4-[3-[(1,1-dimethylethyl)-amino]-2-hydroxypropoxy]-phenyl]-ethenyl]-2H-indol-2-one and its hydrochloride 4.24 g of the base of the product of Example 3 in 60 ml of acetic acid and 1.7 g of N-chlorosuccinimide were stirred under an inert atmosphere for 2 hours. By diluting with water, alkalinizing with ammonia, saturating with potassium carbonate, extracting with ethyl acetate and isolating by chromatography on silica (eluent: ethyl acetate-triethylamine 9-1) the fractions of Rf=0.20, 3.6 g of chlorinated product were obtained.

The said chlorinated product in 50 ml of ethanol and 100 ml of N hydrochloric acid was refluxed for 2 hours with stirring under an inert atmosphere. After cooling, diluting with 200 ml of water, cooling, filtering, washing with ethanol, and drying at 80° C. under reduced pressure to obtain 2.1 g of 1,3-dihydro-4-[2-[4-[3-[(1,1-dimethylethyl)-amino]-2-hydroxypropoxy]-phenyl]-ethenyl]-2H-indol-2-one and its hydrochloride in the form of its hydrochloride melting at ≃280° C.

The mother liquors were made alkaline by the addition of sodium hydroxide and were extracted with ethyl acetate. After purifying by chromatography on silica (eluent: ethyl acetatetriethylamino 9-1), 500 mg of 1,3-dihydro-4-[2-[4-[3-[(1,1-dimethylethyl)-amino]-2-hydroxypropy]-phenyl]-ethenyl]-2H-indol-2-one with its hydrochloride were obtained melting at 110° C.

| Analysis: $C_{23}H_{29}N_2ClO_3$; molecular weight = 416.951 | | | | |
|---|---|---|---|---|
| | % C | % H | % N | % Cl |
| Calculated: | 66.26 | 7.01 | 6.72 | 8.50 |
| Found: | 66.0 | 7.2 | 6.6 | 8.6 |

EXAMPLE 6

N-(1,1-dimethylethyl)-3-[2-[2-(1H-indol-4-yl)-ethenyl]-phenoxy]-propanamine and its succinate

STEP A:

4-[2-[2-(3-chloropropoxy)-phenyl]-ethenyl]-1H-indol

Under an inert atmosphere, 235 mg of 2-[(1H-indol-4-yl)-ethenyl]-phenol in 20 ml of tetrahydrofuran with 0.15 ml of diethyl azodicarboxylate, 0.1 ml of 3-chloro-1-propanol, and 262 mg of triphenylphospine were stirred for 5 hours. Then 0.1 ml of 3-chloro-1-propanol, 0.15 ml of diethyl azodicarboxylate and 262 mg of triphenyl phospine were added, and after 15 hours of stirring at ambient temperature, the mixture was concentrated to dryness. The residue was purified by chromatography on silica (eluent: benzene) to obtain 310 mg of 4-[2-[2-(3-chloropropoxy)-phenyl]-ethenyl]-1H-indol.

STEP B:

N-(1,1-dimethylethyl)-3-[2-[2-(1H-indol-4-yl)-ethenyl]-phenoxy]-propanamine and its succinate 250 mg of product of Step A in solution in 2 ml of dimethylformamide, 2 ml of tert-butylamine and 110 mg of potassium carbonate were heated for 3 hours at 120° C. under a pressure of 5 Kg. After diluting with water, extracting with ethyl acetate and washing with water, 295 mg of a resin were obtained which were purified by chromatography on silica (eluting with ethyl acetate-triethylamine 9-1) to obtain 235 mg of N-(1,1-dimethylethyl)-3-[2-[2-(1H-indol-4-yl)-ethenyl]-phenoxy]-propanamine.

Formation of the succinate 8.9 g of the said base were dissolved in 300 ml of isopropanol and 3 g of succinic acid were added. The mixture was heated to reflux and after concentrating to 200 ml, cooling, filtering and drying under reduced pressure, 8.7 g of the succinate were obtained melting at 200° C.

EXAMPLE 7

1-[(1,1-dimethylethyl)-amino]-3-[3-2-(1H-indol-4-yl)-ethenyl]-phenoxy]-2-propanol and its hydrochloride Using the process of Example 1, m-hydroxybenzyltriphenyl phosphonium was reacted to obtain 1-[(1,1-dimethylethyl)-amino]-3-[3-[2-(1H-indol-4-yl)-ethenyl]-phenoxy]-2-propanol and its hydrochloride in the form of hydrochloride melting at ≃184° C. after crystallization from acetonitrile.

| Analysis: $C_{22}H_{27}N_2ClO_2$; molecular weight = 386.925 | | | | |
|---|---|---|---|---|
| | % C | % H | % N | %Cl |
| Calculated: | 68.29 | 7.03 | 7.27 | 9.16 |
| Found: | 68.0 | 7.0 | 7.1 | 9.0 |

EXAMPLE 8

1-[1,1-dimethylethyl)-amino]-3-[2-[2-(1H-indol-4-yl)-ethyl]-phenoxy]-2-propanol 365 mg of the base of Example 2 were hydrogenated for 1 hour in 20 ml of ethanol in the presence of 100 mg of palladium at 10% on carbon. By filtering and evaporating the solvent at 50° C. under reduced pressure, 325 mg of 1-[(1,1-dimethylethyl)-amino]-3-[2-[2-(1H-indol-4-yl)-ethyl]-phenoxy]-2-propanol were obtained.

| NMR (250 MHz) in CDCl$_3$: | |
|---|---|
| H—tert.-butyl | 275 Hz |
| CH$_2$ in α of the nitrogen, | 685 to 732 Hz |
| CH$_2$ of ethyl | 752 to 802 Hz |
| CH$_2$ in α of oxygen, | 977 to 1025 Hz |

Formation of the hydrochloride 4.5 g of the product obtained above were dissolved in 200 ml of isopropanol and a saturated solution of hydrochloric acid in isopropanol was added. The mixture was concentrated under reduced pressure to a volume of 100 ml, then by cooling, separating and drying at 60° C. under reduced pressure, 4.7 g of the hydrochloride were obtained melting at 105° C.

EXAMPLE 9

1,3-dihydro-4-[2-[2-[3-[(1,1-dimethylethyl)-amino]-2-hydroxypropoxy]-phenyl]-ethenyl]-2H-indol-2-one and its hydrochloride

STEP A: Halogenation

Using the method of Example 5, 10 g of the base obtained in Example 2 were reacted to obtain 6.9 g of the chlorinated derivative.

STEP B:

1,3-dihydro-4-[2-[2-[3-[(1,1-dimethylethyl)-amino]-2-hydroxypropoxy]-phenyl]-ethenyl]-2H-indol-2-one and its hydrochloride 6.9 g of the product of Step A, 100 ml of ethanol and 200 ml of N hydrochloric acid were refluxed for 2 hours and were then diluted with 100 ml of iced water. Alkalinizing by adding sodium hydroxide, extracting with ethyl acetate and chromatographing on silica (eluting with chloroform-acetone-triethylamine 6-3-1), 4.3 g of 1,3-dihydro-4-[2-[2-[3[(1,1-dimethylethyl)-amino]-2-hydroxypropoxy]-phenyl]-ethenyl]-2H-indol-2-one melting at 112° C. were obtained.

Formation of the hydrochloride

The base obtained was dissolved in 200 ml of isopropanol and a saturated solution of hydrochloric acid in isopropanol was added thereto. The mixture was refluxed for 30 minutes and was then concentrated to a volume of 100 ml, separated and dried at 80° C. under reduced pressure to obtain 3.65 g of the hydrochloride melting at >260° C.

| Analysis: C$_{23}$H$_{28}$N$_2$O$_3$, HCl; molecular weight = 416.961 | | | | |
|---|---|---|---|---|
| | % C | % H | % N | % Cl |
| Calculated: | 66.26 | 7.01 | 6.72 | 8.50 |
| Found: | 66.3 | 7.1 | 6.8 | 8.7 |

EXAMPLE 10

1-[(1,1-dimethylethyl)-amino]-3-[2-[2-(1-methyl-1H-indol-4-yl)-ethenyl]-phenoxy]-2-propanol (trans E) and its neutral oxalate A suspension of 9.4 g of the base of Example 2, 100 ml of dimethylformamide and 1.2 g of sodium hydride was heated for 30 minutes at 40° to 50° C. and was then cooled to 0° to 5° C. 1.7 ml of methyl iodide were added after which the mixture was heated again for 3 hours at 40° C. After allowing the temperature to return to ambient, the mixture was diluted with 200 ml of water and was extracted with ethyl acetate. The extracts were washed with water, dried, and the solvent was evaporated at 50° C. under reduced pressure. By chromatographing on silica (eluent: chloroform - acetone-triethylamine 6-3-1), 5 g of the 1-[(1,1-dimethylethyl)-amino]-3-[2-[2-(1-methyl-1H-indol-4-yl)-ethenyl]-phenoxy]-2-propanol (trans E) were obtained.

Formation of the neutral oxalate 5 g of the base obtained above were dissolved in 200 ml of isopropanol and first 1.7 g of oxalic acid and then 500 ml of methanol were added thereto. The mixture was refluxed until solution was complete. After concentrating to a volume of 100 ml cooling, separating and drying at 80° C. under reduced pressure, the product obtained is crystallized from a mixture of ethanol and methanol to obtain 3.9 g of oxalate melting at 225° C.

EXAMPLE 11

N-(1,1-dimethylethyl)-2-[2-[2-(1H-indol-4-yl)-ethenyl]-phenoxy]-ethanamine (trans E) and its acid tartrate

STEP A:

4-[2-[2-[(2-chloro)-ethoxy]-phenyl]-ethenyl]-1H-indole (trans E)

4 g of 2-[(1H-indol-4-yl)-ethenyl]-phenol obtained in Step A of Example 1 in 100 ml of 2N sodium hydroxide after having added 6 g of 2-chloroethanol tosylate were heated for 6 hours at reflux and the mixture was left for 16 hours at ambient temperature, then diluted with water and extracted with ethyl acetate. After eliminating the solvent under reduced pressure and chromatography on silica (eluent: benzene), 2 g of 4-[2-[2-[(2-chloro)-ethoxy]-phenyl]-ethenyl]-1H-indole (trans E) were obtained.

STEP B:

N-(1,1-dimethylethyl)-2-[2-[2-(1H-indol-4-yl)-ethenyl]-phenoxy]-ethanamine (trans E) and its tartrate A mixture of 1.65 g of the product of Step A, 20 ml of dimethylformamide, 15 ml of tert.-butylamine and 770 mg of potassium carbonate was heated for 4 hours at 120° C. and was then diluted with 100 ml of water. The mixture was extracted with ethyl acetate and the extracts were washed with water, dried, concentrated under reduced pressure at 50° C. The residue was chromatographed on silica (eluent: ethyl acetate-triethylamine 9-1) to obtain 1.7 g of N-(1,1-dimethylethyl)-2-[2-[2-(1H-indol-4-yl)-ethenyl]-phenoxy]-ethanamine (trans E).

Formation of the acid tartrate 1.9 g of the said base were dissolved in 200 ml of isopropanol and 100 ml of methanol, then 850 mg of DL tartaric acid were added. The mixture was heated for 30 minutes at reflux and after filtering hot, concentrating, cooling and drying under reduced pressure at 80° C.

2.55 g of the acid tartrate were obtained melting at 180°–182° C.

EXAMPLE 12

Neutral succinate of N-(1,1-dimethylethyl)-3-[2-[2-(1H-indol-4-yl)-ethyl]-phenoxy]-propanamine 2.5 g of the succinate of Example 6 were hydrogenated in 500 ml of methanol in the presence of 850 mg of palladium at 10% on charcoal. After filtering, concentrating under reduced pressure at 50° C. to a volume of 50 ml, cooling, filtering and drying under reduced pressure, 2.25 g of neutral succinate of N-(1,1-dimethylethyl)-3-[2-[2-(1H-indol-4-yl)-ethyl]-phenoxy]-propanamine melting at 190° C. were obtained.

EXAMPLE 13

N-[2-[2-[2-(1H-indol-4-yl)-ethyl]-phenoxy]-ethyl]-2-methyl-2-propanamine and its acid tartrate Using the procedure of Example 8, 550 mg of the product of Step B of Example 11, were reacted to obtain 643 mg of N-[2-[2-[2-(1H-indol-4-yl)-ethyl]-phenoxy]-ethyl]-2-methyl-2-propanamine which was purified by chromatography on silica (eluent: cyclohexane-chloroform-triethylamine 6-3-1) for 510 mg of pure product.

Formation of the acid tartrate 1.7 g of the said base were dissolved in 200 ml of isopropanol and 760 mg of DL tartaric acid were added. The mixture was heated for 15 minutes at reflux. After filtering, concentrating to a volume of 100 ml, cooling, separating and drying at 80° C. under reduced pressure, 1.75 g of the acid tartrate melting at 158° C. were obtained.

| Analysis: $C_{22}H_{28}N_2O.C_4H_6O_4$; molecular weight = 486.57 | | | |
|---|---|---|---|
| | % C | % H | % N |
| Calculated: | 64.18 | 7.04 | 5.76 |
| Found: | 63.9 | 7.3 | 5.8 |

EXAMPLE 14

N-[2-[2-[2-(1H-indol-4-yl)-ethenyl]-phenoxy]-ethyl]-benzeneethanamine (E) and its neutral fumarate 8.8 ml of 2-phenylethylamine were added to a solution of 3.48 g of the product of Step A of Example 11 in 25 ml of ethanol and the mixture was refluxed for 28 hours. The reaction mixture was cooled and poured into water and was extracted with ether. The extracts were washed with water, with an aqueous solution of sodium chloride, dried and concentrated to dryness. The residue was chromatographed on silica (eluent: cyclohexane-chloroform-triethylamine 6-3-1) to obtain 3.54 g of N-[2-[2[2-(1H-indol-4-yl)-ethenyl]-phenoxy]-ethyl]-benzene-ethanamine (E).

Preparation of the neutral fumarate

A solution of 0.24 g of fumaric acid in 15 ml of ethanol was added to 1.61 g of the said base in solution in 32 ml of ethanol and the mixture was stirred for 90 minutes. After filtering, rinsing with ethanol and drying, 1.41 g of neutral fumarate were obtained which was crystallized from methanol to obtain 0.71 g of pure product melting at 184°–185° C.

| Analysis: $C_{26}H_{26}N_2O$, $\frac{1}{2}C_4H_4O_4$; molecular weight = 881.085 | | | |
|---|---|---|---|
| | % C | % H | % N |
| Calculated: | 76.33 | 6.4 | 6.35 |
| Found: | 76.0 | 6.5 | 6.4 |

EXAMPLE 15

N-[2-[2-[2-(1H-indol-4-yl)-ethyl]-phenoxy]-ethyl]-benzene ethanamine and its hydrochloride 3.54 g of the base of Example 14 were hydrogenated in 110 ml of ethanol in the presence of 1.18 g of palladium at 10% on charcoal, then, by filtering and eliminating the solvent under reduced pressure, 3.32 g of N-[2-[2-[2-(1H-indol-4-yl)-ethyl]-phenoxy]-ethyl]-benzene ethanamine were obtained.

Preparation of the hydrochloride 3.2 g of the said base were dissolved in 65 ml of isopropanol and an excess of a saturated solution of hydrochloric acid in ethyl acetate was added to it. Crystallization was initiated, followed by cooling, filtering and drying under reduced pressure to obtain 2.8 g of the hydrochloride which was crystallized from isopropanol to obtain 1.64 g of pure product melting at 177°–178° C.

| Analysis: $C_{26}H_{28}N_2O$, HCl; molecular weight = 420.991 | | | | |
|---|---|---|---|---|
| | % C | % H | % N | % Cl |
| Calculated: | 74.17 | 6.94 | 6.65 | 8.42 |
| Found: | 73.9 | 7.0 | 6.6 | 8.6 |

Using the process, there can also notably be prepared:
N-[2-[2-[2-(1H-indol-4-yl)-ethyl]-phenoxy]-ethyl]-dimethylamine,
N-[2-[2-[2-(1H-indol-4-yl)-ethenyl]-phenoxy]-ethyl]-dimethylamine
N-[2-[2-[2-(1H-indol-4-yl)-ethyl]-phenoxy]-ethyl]-diethylamine,
N-[2-[2-[2-(1H-indol-4-yl)-ethenyl]-phenoxy]-ethyl]-diethylamine
N-[2-[2-[2-(1H-indol-4-yl)-ethyl]-phenoxy]-ethyl]-piperidine and
N-[2-[2-[2-(1H-indol-4-yl)-ethenyl]-phenoxy]-ethyl]-piperidine
and their non-toxic, pharmaceutically acceptable acids salts.

EXAMPLE 16

Tablets were prepared containing 20 mg of the product of Example 3 (hydrochloride) or 50 mg of the hydrochloride of Example 2 and excipient of lactose, starch, talc, magnesium stearate q.s. for a tablet weight of 100 mg.

PHARMACOLOGICAL STUDY

A. Anti-calcic activity in vitro

Rat caudal arteries were cut into a spiral and were attached to tension sensors and were kept in tanks of 25 $\mu$l of Krebs buffer-sodium bicarbonate (NaCl: 120.8 mM, KCl: 5.9 mM, MgCl$_2$: 1.2 mM, NaH$_2$PO$_4$: 1.2 mM, NaHCO$_3$: 15.5 mM, glucose: 12.6 mM) at 37° C. gassed with a mixture of O$_2$: 95% - CO$_2$: 5%. The preparations were depolarized with a buffer solution with a concentration of 100 mM in K$^+$ions (NaCl: 26.7 mM, KCl: 100 mM, MgCl$_2$: 1.2 mM, NaH$_2$PO$_4$: 1.2 mM, NaHCO$_3$:

15.5 mM, glucose: 12.6 mM). Calcium chloride was added in a volume of 250 μl to obtain a range of increasing concentrations of $Ca^{2+}$ ions from 0.1 to 3.0 mM. The contractions of the arteries were recorded and a control range was established in this way. The operation was repeated every 15 minutes with the $Ca^{2+}$ range of ions and the preparation was washed four times after each range.

When a stable response had been obtained, the operation with the range of $Ca^{2+}$ ions was carried out in the presence of different concentrations of the product under test until a stable response was obtained. The contractions of the arteries depend on the entry of the $Ca^{2+}$ ions into the cells of the smooth muscles and are caused by the depolarization of the smooth muscle by the $K^+$ ions and by the action of the noradrenaline liberated at the presynaptic level. By repeating the operation with the arteries denervated by the action of 6-OH dopamine, the specific action due to the noradrenaline was suppressed. The results were expressed in IC 50 (inhibiting concentration 50), which is the concentration of the product under test which inhibits by 50% the concentration due to the $K^+$ ions According to the results in the following table, it can be seen that the products of the present application possess a strong anti-calcic activity.

| Product of Example | IC 50 in μM |
| --- | --- |
| 1 | 4.0 |
| 2 | 1.2 |
| 3 | 0.6 |
| 4 | 3.5 |
| 5 | 2.5 |
| 6 | 2 |
| 8 | 1.5 |
| 9 | 1.4 |
| 12 | 0.3 |

B. Anti-arrhythmic activity in rats

Male rats weighing 300–350 g anesthetized by intraperitoneal route with 1.20 g/Kg of urethane were tracheotomized and submitted to artifical respiration (40–50 insufflations of 3 ml/minute). Needles were implanted sub-cutaneously to record the electro-cardiogram of the rats on the signal in derivation DII. The products under test were administered by intravenous route.

Five minutes after the product was administered, the jugular vein of the rats was perfused with 10 μg/min. of an aconitine solution and the time of appearance of disorders of the cardiac rhythm was noted. The results were expressed in percentage of the extension of the time of appearance of disorders of the cardiac rhythm in comparison with controls and as a function of the dose of the product under test. The results in the following table show that certain products of the application are endowed with good anti-arrhythmic properties.

| Product of Example | Dose | Percentage of extension of time |
| --- | --- | --- |
| 2 | 10 mg/Kg | 110% |
|  | 5 mg/Kg | 30% |
| 6 | 5 mg/Kg | 49% |
| 8 | 5 mg/Kg | 162% |
| 9 | 5 mg/Kg | 167% |
| 11 | 5 mg/Kg | 41% |

C. Hypotensive activity

The hypotensive activity was studied on male rats of Wistar strain weighing about 300 g and anesthetized with 50 mg/Kg by intravenous route of sodium pentobarbital. The product tested was administered by intravenous route in the jugular vein and the pressure in the carotid artery was measured before and after administration of the product tested. The following table reports the variations expressed in percentage of the arterial pressure after administration of the product tested by comparison with the initial control arterial pressure.

|  |  | % Variation of the arterial pressure | | | |
| --- | --- | --- | --- | --- | --- |
| Product of Example | Dose mg/Kg | 1 min. after administration | 5 min. after administration | 10 min. after administration | 30 min. after administration |
| 1 | 1 | −11 | −11 | −12 | −13 |
| 2 | 1 | −17 | −10 | −10 | −14 |

D. $\alpha_2$- adrenergic receptor affinity 10 cortices removed from the brains of male rats weighing on the average 150 mg were homogenized in 90 ml of 0.32 M sucrose and after centrifuging the homogenized mixture at 1,000 g for 10 minutes at 0° C., the supernatant was centrifuged at 30,000 g for 10 minutes at 0° C. to +4° C. The residue was suspended in 240 ml of Tris HCl 50 mM buffer, pH 7.7 and centrifuged at 30,000 g for 15 minutes at 0° to +4° C. The new residue obtained was suspended in 480 ml of $NaKPO_4$ 50 mM buffer, pH 7.4. Then, 2 ml of suspension were incubated for 45 minutes at 25° C. in the presence of $^3H$ rauwolscine at a concentration of 0.15 mM:
(i) alone
(ii) with increasing concentrations of the product under test, or
(iii) to determine the non-specific fixation, with non-radioactive phentolamine at a concentration of $10^{-5}$ M.

The incubated suspensions were filtered on Whatman GF/C and the filters were washed three times with 5 ml of $NaKPO_4$ buffer, pH 7.4, at 0° C. The radio-activity of the filters was measured by liquid scintillation. The affinity of the product under test for the $\alpha_2$- adrenergic receptors were given relative to phentolamine as reference product. CD=concentration of phentolamine inhibiting 50% of the specific fixation of $^3H$ rauwolscine:

CX=concentration of the product under test inhibiting 50% of the specific fixation of $^3H$ rauwolscine. The relative affinity was given by the relation : ARL=100 CD/CX The following results were obtained:

| Product of Example | ARL in % |
| --- | --- |
| 1 | 0.1 |
| 2 | 0.25 |
| 3 | 0.7 |
| 4 | 0.0 |

These results show that the products of the application offer a notable affinity for the $\alpha_2$- adrenergic receptors.

E. β₁- adrenergic receptor affinity 10 cortices removed from the brains of rats weighing on the average 150 g were homogenized in 90 ml of 0.32 M sucrose and after centrifuging the homogenized mixture at 1,000 g for 20 minutes at 0° C., the supernatant was centrifugated at 30,000 g for 15 minutes at 0° C. to +4° C. The residue was suspended in 120 ml of Tris HCl 50 mM buffer pH 7.7 and centrifuged at 30,000 g for 15 minutes at 0° C. to +4° C. The new residue obtained was suspended in 480 ml of Krebs Tris HCl 50 mM buffer, 7.7 pH. Then, 2 ml of the suspension were incubated for 10 minutes at 37° C. in the presence of ³H dihydroalprenolol at a concentration of $10^{-9}$ M:

(i) alone,
(ii) with increasing concentrations of the product under test, or
(iii) to determine the non-specific fixation, with non-radioactive propranolol at a concentration of $10^{-5}$ M.

The incubated suspensions were filtered on Whatman GF/C and the filters were washed three times with 5 ml of Krebs Tris HCl buffer pH 7.7 at 0° C. The radioactivity of the filters was measured by liquid scintillation. The affinity of the product for the adrenergic receptors was given relative to propranolol as reference product, CD = concentration of propranolol inhibiting 50% of the specific fixation of the ³H dihydroalprenolol: CX = concentration of the product under test inhibiting 50% of the specific fixation of the ³H dihydroalprenolol. The relative affinity was given by the relation ; ARL=100 CD/CX The following results were obtained:

| Product of Example | ARL in % |
|---|---|
| 1 | 92.5 |
| 2 | 198 |
| 3 | 0.8 |
| 4 | 1.0 |

These results show that the products of the application offer a notable affinity for β₁- adrenergic receptors.

F. β₂- adrenergic receptor affinity

The cerebelli removed from the brains of male rats weighing on the average 150 g were homogenized in 90 ml of 0.32 M sucrose and after centrifuging the homogenized mixture at 1,000 g for 20 minutes at 0° C., the supernatant was centrifuged at 30,000 g for 15 minutes at 0° C. to +4° C. The residue was suspended in 120 ml of Tris HCl 50 mM buffer pH 7.7, and centrifuged at 30,000 g for 15 minutes at 0° to +4° C. The new residue obtained was suspended in 480 ml of Krebs Tris HCl buffer, pH 7.7. 2 ml of the suspension were then incubated at 37° C. for 10 minutes in the presence of 3H dihydroalprenolol at a concentration of $10^{-9}$ M:

(i) alone,
(ii) with increasing concentrations of the product under test
(iii) to determine the non-specific fixation, with non-radio-active propranolol at a concentration of $10^{-5}$ M. The incubated suspensions were filtered on Whatman GF/C and the filters were washed three times with 5 ml of Krebs Tris HCl buffer pH 7.7 at 0° C.

The radio-activity of the filters was measured by liquid scintillation. The affinity of the test product for β₂- adrenergic receptors was given relative to propranolol as reference product.

CD = concentration of propranolol inhibiting 50% of the specific fixation of ³H dihydroalprenolol:

CX = concentration of the product under test inhibiting 50% of the specific fixation of the ³H dihydroalprenolol. The relative affinity was given by the relation: ARL=100 CD/CX The following results were obtained.

| Product of Example | ARL in % |
|---|---|
| 1 | 18 |
| 2 | 172 |
| 3 | 0.1 |
| 4 | 0.03 |

These results show that the products of the application have a notable affinity for the β₂- adrenergic receptors.

G. Acute toxicity

The lethal doses LD₀ for the different test compounds were evaluated after oral administration to mice and the maximum dose not causing any mortality in 8 days was called LD₀. The following results were obtained:

| Product of Example | LD₀ in mg/Kg |
|---|---|
| 1 | >100 |
| 2 | >100 |
| 3 | >100 |
| 4 | 60 |
| 5 | >100 |
| 6 | >400 |
| 8 | >400 |
| 11 | 200 |

Various modifications of the products and process of the invention may be made without departing from the spirit or scope thereof and it is to be understood that the invention is intended to be limited only as defined in the appended claims.

What we claim is:

1. A compound selected from the group consisting of ethenylphenol indoles of the formula

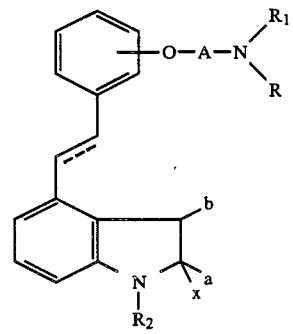

wherein R and R₁ are individually selected from the group consisting of hydrogen, alkyl of 1 to 5 carbon atoms, cycloalkyl of 3 to 7 carbon atoms, cycloalkylalkyl of 4 to 7 carbon atoms and carbocyclic aralkyl of 7 to 12 carbon atoms optionally substituted with 1 to 3 members of the group consisting of halogen, methyl, ethyl, methoxy, ethoxy, methylthio, —CF₃, —NH₂ and —NO₂ or R and R₁ together with the nitrogen atom form a heterocycle selected from the group consisting of pyrrolidino, piperidino, morpholino, piperazinyl, methylpiperazinyl, ethylpiperazinyl and propylpiperazinyl, a together with X is =O and b is hydrogen or a together with b is a carbon-carbon bond and X is hydrogen, the dotted line indicates the possibility of a double bond with the compounds having the trans configuration if a double bond, A is selected from the group consisting of

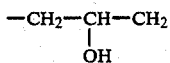

and —(CH₂)$_n$—, n is 2, 3, 4 or 5, R₂ is selected from the group consisting of hydrogen and alkyl of 1 to 5 carbon atoms with the proviso that R and R₁ are not both hydrogen when A is

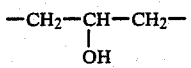

and their non-toxic, pharmaceutically acceptable acid addition salts.

2. A compound of claim 1 wherein R₂ is hydrogen, A is

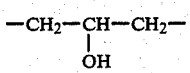

and R and R₁ are individually selected from the group consisting of hydrogen and alkyl of 1 to 5 carbon atoms with the proviso they are not both hydrogen.

3. A compound of claim 1 wherein R₂ is hydrogen, A is —(CH₂)$_n$— and R and R₁ are individually selected from the group consisting of hydrogen and alkyl of 1 to 5 carbon atoms.

4. A compound of claim 1 wherein

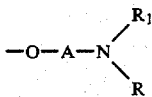

is in the ortho position.

5. A compound of claim 1 wherein R is hydrogen and a and b form a carbon-carbon bond.

6. A compound of claim 1 selected from the group consisting of 1-[(1,1-dimethylethyl)-amino])-3-[4-[2-(1H-indol-4-yl)-ethenyl]-phenoxy]-2-propanol and its non-toxic, pharmaceutically acceptable acid addition salts.

7. A compound of claim 1 selected from the group consisting of 1-[(1,1-dimethylethyl)-amino]-3-[2-[2-(1H-indol-4-yl)-ethyl]-phenyl]-2-propanol, and its non-toxic, pharmaceutically acceptable acid addition salts.

8. A compound of claim 1 selected from the group consisting of 1,3-dihydro-4-[2-[2-[3-[(1,1-dimethylethyl)-amino]-2-hydroxy-propoxy]-phenyl]-ethenyl]-2H-indol-2-one and its non-toxic, pharmaceutically acceptable acid addition salts.

9. A compound of claim 1 selected from the group consisting of N-(1,1-dimethylethyl)-3-[2-[2-(1H-indol-4-yl)-ethyl]-phenoxyl]-propanamine and its non-toxic, pharmaceutically acceptable acid addition salts.

10. An antiarythmic composition comprising an antiarythmically effective amount of at least one compound of claim 1 and a pharmaceutical carrier.

11. A composition of claim 10 wherein R₂ is hydrogen, A is

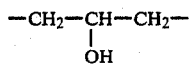

and R and R₁ are individually selected from the group consisting of hydrogen and alkyl of 1 to 5 carbon atoms with the proviso they are not both hydrogen.

12. A composition of claim 10 wherein R₂ is hydrogen, A is —(CH₂)$_n$— and R and R₁ are individually selected from the group consisting of hydrogen and alkyl of 1 to 5 carbon atoms.

13. A composition of claim 10 wherein

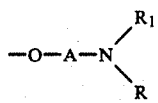

is in the ortho position.

14. A composition of claim 10 wherein R is hydrogen and a and b form a carbon-carbon bond.

15. A composition of claim 10 wherein the compound is selected from the group consisting of 1-[(1,1-dimethylethyl)-amino]-3-[4-[2-(1H-indol-4-yl)-ethenyl]-phenoxy]-2-propanol and its non-toxic, pharmaceutically acceptable acid addition salts.

16. A composition of claim 10 wherein the compound is selected from the group consisting of 1-[(1,1-dimethylethyl)-amino]-3-[2-[2-(1H-indol-4-yl)-ethyl]-phenoxy]-2-propanol and its non-toxic, pharmaceutically acceptable acid addition salts.

17. A composition of claim 10 wherein the compound is selected from the group consisting of 1,3-dihydro-4-[2-[2-[3-(1,1-dimethylethyl)-amino]-2-hydroxy-propoxy]-phenyl]-ethenyl]-2H-indol-2-one and its non-toxic, pharmaceutically acceptable acid addition salts.

18. A composition of claim 10 wherein the compound is selected from the group consisting of N-(1,1-dimethylethyl)-3[2-[2-(1H-indol-4-yl)-ethyl]-phenoxy]-propanamine and its non-toxic, pharmaceutically acceptable acid addition salts.

19. A method of treating arythmia in warm-blooded animals comprising administering to warm-blooded animals an anti-arythmially effective amount of at least one compound of claim 1.

20. A method of claim 19 wherein R₂ is hydrogen, A is

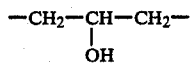

and R and R₁ are individually selected from the group consisting of hydrogen and alkyl of 1 to 5 carbon atoms with the proviso they are not both hydrogen.

21. A method of claim 19 wherein R₂ is hydrogen, A is —(CH₂)₂— and R and R₁ are individually selected from the group consisting of hydrogen and alkyl of 1 to 5 carbon atoms.

22. A method of claim 19 wherein

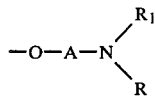

is in the ortho position.

23. A method of claim 19 wherein R is hydrogen and a and b form a carbon-carbon bond.

24. A method of claim 19 wherein the compound is selected from the group consisting of 1-[(1,1-dimethylethyl)-amino]-3-[4-[2-(1H-indol-4-yl)-ethenyl]-phenoxy]-2-propanol and its non-toxic, pharmaceutically acceptable acid addition salts.

25. A method of claim 19 wherein the compound is selected from the group consisting of 1-[(1,1-dimethylethyl)-amino]-3-[2-[2-(1H-indol-4-yl)-ethyl]-phenoxy]-2-propanol and its non-toxic, pharmaceutically acceptable acid addition salts.

26. A method of claim 19 wherein the compound is selected from the group consisting of 1,3-dihydro-4-[2-[2-[3-(1,1-dimthylethyl)-amino]-2-hydroxy-propoxy]-phenyl]-ethenyl]-2H-indol-2-one and its non-toxic, pharmaceutically acceptable acid addition salts.

27. A method of claim 19 wherein the compound is selected from the group consisting of N-(1,1-dimethylethyl)-3-[2-[2-(1H-indol-4-yl)-ethyl]-phenoxy]-propanamine and its non-toxic, pharmaceutically acceptable acid addition salts.

* * * * *